United States Patent [19]
Thornton et al.

[11] Patent Number: 6,061,588
[45] Date of Patent: May 9, 2000

[54] CATHETER APPARATUS FOR POSITIONING A WIRE

[75] Inventors: Richard T. Thornton, League City; Ross Baker, Houston, both of Tex.

[73] Assignee: Advanced Cardiovascular Systems, Inc., Santa Clara, Calif.

[21] Appl. No.: 09/162,733

[22] Filed: Sep. 29, 1998

[51] Int. Cl.[7] .......................................................... A61B 5/05
[52] U.S. Cl. ............................................ 600/424; 600/585
[58] Field of Search ................................ 600/1, 373, 374, 600/381, 424, 434, 435, 547, 585

[56] References Cited

U.S. PATENT DOCUMENTS

| | | | |
|---|---|---|---|
| 5,386,828 | 2/1995 | Owens et al. | 600/424 |
| 5,513,637 | 5/1996 | Twiss et al. | 600/424 |
| 5,910,101 | 6/1999 | Andrews et al. | 600/3 |
| 5,938,603 | 8/1999 | Ponzi | 600/424 |

FOREIGN PATENT DOCUMENTS

| | | | |
|---|---|---|---|
| 2263641 | 8/1993 | United Kingdom | 600/585 |

*Primary Examiner*—Max Hindenburg
*Attorney, Agent, or Firm*—Blakely, Sokoloff, Taylor & Zafmann LLP

[57] ABSTRACT

A method and apparatus for positioning a radioactive portion of a wire at one or more positions within the lumen of a guide catheter, such as for intravascular radiotherapy, are disclosed. The method and the apparatus provide for better positioning the radioactive portion in light of bunching of the wire within the lumen during insertion. A computerized controller uses a monitoring device to control an afterloader's insertion and withdrawal of the wire into the guide catheter. The guide catheter includes a sensor at its distal end, the sensor being an electrical contact having conductive surfaces exposed within the lumen and outside the guide catheter. The wire is electrically conductive, and is configured to come into contact with the sensor's conductive surface within the lumen when the wire is fully inserted into the lumen. The monitoring device includes one lead connected to the wire and a second lead connected to the subject's body. The monitoring device is configured to use an alternating current signal to sense a closed circuit extending sequentially through a signal path including the wire, the sensor, and the subject's body, when the wire comes into contact with the sensor.

The computer controller directs the afterloader to insert the wire into the lumen until a closed circuit is sensed. The controller then directs the afterloader to controllably withdraw the wire until the circuit is broken, thus removing any bunching from the wire. The wire then can be maintained in position at the end of the lumen to irradiate the subject. The wire also may be withdrawn by prescribed amounts to other positions within the lumen, to treat the subject at these locations.

35 Claims, 3 Drawing Sheets

CATHETER APPARATUS FOR POSITIONING A WIRE

BACKGROUND OF THE INVENTION

This invention relates generally to catheter-type apparatus for use in treating a subject, and, more particularly, to a device and a related method for positioning a wire along a guide catheter.

Numerous forms of brachytherapy, such as intravascular radiotherapy, involve inserting a guide catheter within a subject, followed by inserting a wire within a lumen in the guide catheter. In some medical uses, the position of a longitudinal portion of the wire, with respect to the portion of the subject's body that requires treatment, can be is critical. Furthermore, accurate control through a plurality of such positions can likewise be critical.

For example, typical intravascular radiotherapy is performed by advancing a flexible guide catheter through a subject's cardiovascular system until the catheter's distal tip is located immediately past the vessel region to be treated, e.g., the region previously subjected to an angioplasty procedure. The guide catheter can be precisely located with respect to the vessel region using known external scanning techniques. An afterloader then advances a wire, having a radiation source at or near its tip (i.e., a radiation source wire), along a lumen of the guide catheter until the radiation source is positioned proximate to the vessel region to be treated.

The radiation source is held in this region for a prescribed time period that is calculated to deliver an effective dosage of radiation to the region. If the region to be treated is longer than the radiation source can effectively treat from one position, the radiation source is longitudinally moved to a second position, generally immediately adjacent to the previous position, to irradiate a second region of the vessel. After another interval, additional movements may be made to irradiate other areas to be treated. When the areas have all been irradiated, the source wire is withdrawn back into the afterloader.

Precisely positioning the wire's radiation source within the guide catheter, however, is problematic. The precise insertion position of the radiation source depends on the length of wire extending into the lumen, the circumference and length of the lumen, and the amount of bunching up that occurs due to the clearance between the wire and the guide catheter. While the guide catheter can be manufactured with precise tolerances, the amount of bunching (i.e., excessive curvature) on any given insertion depends on many factors, and is not easily determined. Furthermore, the amount of bunching can change during the movement of the wire between positions, further adding to the difficulty.

One method previously used to compensate for this problem is to overshoot the desired position with the radiation source, and then withdraw the wire to back the radiation source into the one or more positions. First, the wire is inserted into the guide catheter far enough to cause the radiation source to definitely overshoot its target position. Next, the wire is pulled back to straighten out (unbunch) the wire to remove the excess curvature and pull the radiation source to its first desired position. The wire is again pulled by prescribed amounts to reach other desired positions. This method, however, requires a guide catheter with a lumen that extends past the target position(s), providing room for the wire to overshoot the target position(s). This precludes having a target position at or near the end of the guide catheter. This limitation becomes critical when using the guide catheter in particularly small or delicate locations, such as coronary arteries, where little room exists for a guide catheter to extend beyond the treatment region.

This problem is typical in forms of brachytherapy involving the precise insertion of a wire within a guide catheter's lumen. Accordingly, there has existed a definite need for a device and a related method for positioning a longitudinal portion of a wire within a guide catheter. The present invention satisfies these and other needs, and provides further related advantages.

SUMMARY OF THE INVENTION

The present invention provides a method of positioning a longitudinal portion of a wire at one or more positions within a guide catheter, and a related apparatus used for performing the method. The invention is useful for irradiating a selected portion of a subject's body, i.e., for brachytherapy. The invention may also be useful for various imaging technologies. It further provides for one of the positions to be at or near a distal end of the guide catheter.

The apparatus includes a monitoring device and a catheter assembly, the catheter assembly having a guide catheter and a treatment wire. The guide catheter, which is appropriately sized to be inserted into the subject, defines a lumen having a cross-sectional size equal to or larger than the minimum necessary to allow passage of the treatment wire throughout the lumen. The treatment wire is preferably configured with a radioactive treatment portion at a distal end of the wire. The treatment portion is configured to be inserted into the lumen to a predetermined treatment position, having the necessary size, shape and flexibility.

The guide catheter features a sensor, configured to work with the monitoring device, to detect the presence of a predetermined portion of the treatment wire at a predetermined longitudinal position along the guide catheter. Preferably, the predetermined portion of the treatment wire is the treatment wire's distal tip. Also, preferably the predetermined longitudinal position within the guide catheter is at the distal end of the lumen, which preferably extends to the distal end of the guide catheter.

The method of the invention entails inserting the guide catheter to a selected location within the subject's body, the selected location preferably being a portion of the subject's cardiovascular system requiring radiation therapy. The treatment wire is then advanced along the guide catheter's lumen while the monitoring device monitors the sensor to determine when the predetermined portion of the treatment wire reaches the predetermined position within the lumen. The advancement is terminated is then stopped at that location. Typically, the advancing of the treatment wire will cause the wire to bunch up within the lumen, causing the wire to curve around within the lumen in excess of the reasonably necessary amount.

The treatment wire is then controllably withdrawn from the lumen while further monitoring the sensor to determine when the predetermined portion of the treatment wire departs from the predetermined position within the lumen. The controlled withdrawal is terminated when the predetermined portion of the treatment wire has, in fact, departed from the predetermined position within the lumen.

This partial withdrawal of the treatment wire straightens it to reduce and/or effectively eliminate its bunching. Preferably, the guide catheter is inserted within the subject such that the position where the controlled withdrawal is terminated is appropriate for the treatment wire's treatment portion (i.e., the radioactive portion) to irradiate the portion of the subject's cardiovascular system requiring radiation therapy. If, in fact, the guide catheter is so inserted, then the treatment wire is maintained in this position for a prescribed treatment time period.

Now, using this position at the guide catheter's distal end as a reference position, the treatment wire may optionally be withdrawn from the lumen by a prescribed amount to another (or a first) treatment position, and then maintained at that position for a prescribed treatment period. These steps may be repeated, with the wire being withdrawn to additional treatment positions for additional prescribed treatment periods.

The insertion and withdrawal of the treatment wire are controlled by a computerized controller using information from the monitoring device. The monitoring device preferably monitors the electrical resistance between the sensor and the treatment wire to establish the presence of the predetermined portion of the treatment wire along the predetermined longitudinal position of the guide catheter. The sensor and treatment wire preferably work together as a switch, forming a complete signal path when in contact, and breaking the signal path when not in contact. The monitoring device preferably monitors the signal path by applying a voltage to pass an ac signal along the signal path.

The signal path extends between a first and second lead of the monitoring device. The first lead preferably connects to a proximal portion of the treatment wire, which is preferably electrically conductive from its proximal portion to its predetermined portion (e.g., its distal tip). The second lead preferably connects indirectly to the sensor, which is an electrical contact having an exposed conductive surface within the lumen. The treatment wire's predetermined portion is preferably configured to contact the sensor's conductive surface within the lumen to close the circuit between the first and second leads, causing the sensor to detect the presence of the predetermined portion of the treatment wire by the electrical connection that is formed, and allowing the monitoring device to establish the presence of the predetermined portion of the treatment wire at the sensor.

The monitoring device's second lead preferably connects to the sensor via an external probe that contacts the subject's body. The sensor preferably includes a conductive surface exposed on the exterior of the guide catheter to contact to the body, completing the signal path through the subject's body and external probe. The signal path thus extends from the first lead through the treatment wire, the sensor, the subject s body and the external probe, to the second lead, and therefore the signal is carried by a portion of the subject's body.

Some of the invention's features provide for accurate positioning of the wire at the distal end of the lumen. Likewise, some of the invention's features provide for the accurate positioning of the wire at other locations by referencing them to the distal end of the lumen. Thus, the lengths of the lumen and catheter are not critical, and do not require exceptionally high manufacturing tolerances.

Other features and advantages of the invention will become apparent from the following detailed description of the preferred embodiments, taken in conjunction with the accompanying drawings, which illustrate, by way of example, the principles of the invention.

DETAILED DESCRIPTION OF THE PREFERRED EMBODIMENTS

Figure 1:
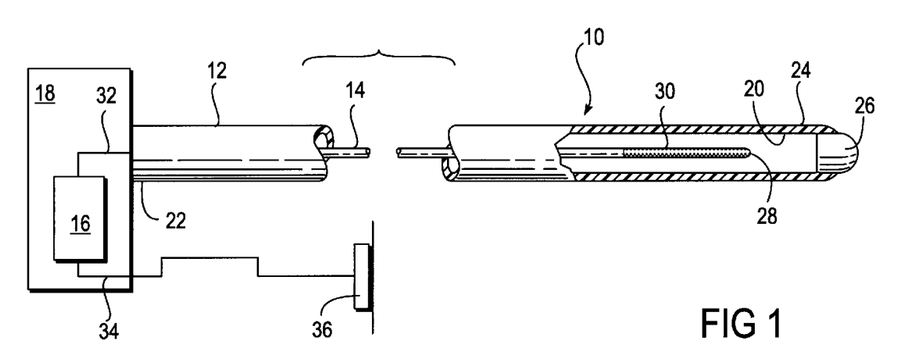
FIG. 1 is a schematic representation of a catheter assembly embodying features of the present invention.

A catheter assembly 10 according to one embodiment of the present invention is shown in FIG. 1. The catheter assembly includes a guide catheter 12 and a treatment wire 14, and it is used with a monitoring device 16 configured to establish and determine the presence of a predetermined portion of the wire (e.g., its distal tip) at a predetermined longitudinal position along the guide catheter (e.g., its distal end).

FIG. 1 depicts the catheter assembly 10 attached to an afterloader 18. The guide catheter 12 has a blind lumen 20 extending from an opening in a proximal end 22 of the guide catheter to a sealed distal end 24 of the guide catheter. The guide catheter's proximal end attaches to the afterloader in a configuration such that the afterloader can insert and advance the treatment wire 14 into the lumen, as is known in the art. While the figure depicts a treatment wire that is slender in comparison to the lumen (for illustrative purposes), the treatment wire will commonly fill roughly 90% of the cross-sectional area of the lumen.

Principally composed of a strong, flexible, nonconducting plastic, the guide catheter 12 includes a metal, or otherwise electrically conductive, distal tip 26 at its distal end 24. A portion of the guide catheter's distal tip forms a surface that is exposed within the lumen at the distal end of the lumen. Another portion of the guide catheter's distal tip forms a surface that is exposed on the outer surface of the guide catheter. Thus, the guide catheter's distal tip forms an electrical contact that electrically connects a surface within the lumen, at the lumen's distal end, to a surface on the exterior of the guide catheter that contacts a subject's body when the guide catheter is in use.

The afterloader 18 is configured to advance a distal tip 28 of the treatment wire 14 along the guide catheter's lumen 20. The afterloader can include a computer control system (not shown) that controls the advancement and withdrawal of the treatment wire in the guide catheter.

A radioactive treatment portion 30 is located on the treatment wire 14 at or near its distal tip. The treatment wire is preferably made of metal, and is thus electrically conductive from a proximal end through its distal tip 28.

The monitoring device 16 monitors a signal path extending between a first lead 32, which is connected to the proximal end of the treatment wire 14, and a second lead 34, which is connected to an external probe 36 that is configured to form an electrical connection to the subject's body (not shown). The monitoring device is capable of monitoring the signal path to determine when the path forms an electrical circuit between the two leads, such as would occur when the treatment wire's distal tip 28 contacts the guide catheter's distal tip 26, the guide catheter's distal tip contacts the subject's body, and the subject's body contacts the external probe. Thus, the monitoring device is configured to establish and determine the presence of the distal tip of the treatment wire at the distal tip of the guide catheter, and the guide catheter's distal tip serves as a sensor configured to sense and detect the presence of (i.e., contact with) the treatment wire. Alternate, and less preferable embodiments of the sensor and monitoring device may be configured to detect the presence of the predetermined portion of the treatment wire by detecting its arrival and/or departure, rather than by having a continual monitoring of the predetermined portion's actual proximity.

While the preferred sensor is an electrical contact that works as a switch in combination with a conductive treatment wire, other sensors, located either on the guide catheter or the treatment wire, are within the scope of the invention. For example, a contact switch could be formed entirely on either the guide catheter or the treatment wire.

Alternately, the sensor could detect the presence of the predetermined portion of the treatment wire at the predetermined location along the guide catheter by visual detection, ultrasonic detection, chemical detection, or any other reasonable detection means.

Figure 2:
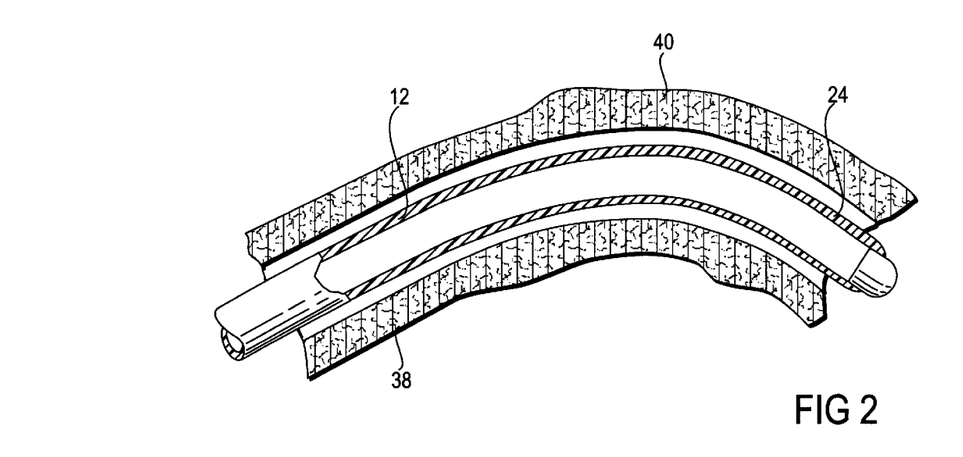
FIG. 2 is a cross-sectional view of a portion of a guide catheter from the catheter assembly depicted in FIG. 1, after insertion within a subject's vascular system.

The catheter assembly 10 can be used in a method for positioning the radioactive treatment portion 30 of the treatment wire 14 within the lumen 20, such as for intravascular radiotherapy. As seen in FIG. 2, the guide catheter 12 is inserted to a selected location within a vessel 38 of the subject's cardiovascular system. The vessel includes a specific length of vascular area 40 requiring radiotherapy.

The distal end 24 of the guide catheter 12 is located within the vascular area 40 requiring radiotherapy, such that the distal end of the lumen defines the desired position of one end of the radiation source 30 during treatment. Conventional methods, such as the use of radio-opaque markers, can be used for locating of the guide catheter.

Figure 3:
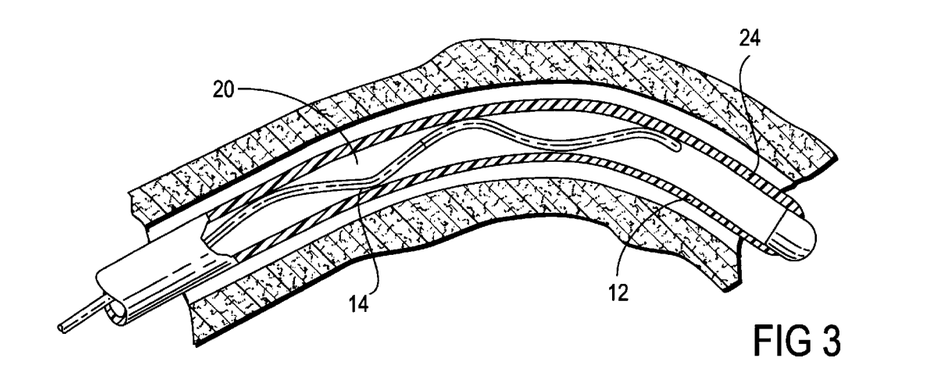
FIG. 3 is the cross-sectional view of the guide catheter depicted in FIG. 2, with a treatment wire being inserted into the guide catheter.

The treatment wire 14 (not shown in FIG. 2) is configured with its radioactive treatment portion 30 having the proper length to irradiate the vascular area 40 requiring radiation treatment, either in one position or a plurality of positions. In use, and as seen in FIG. 3, the afterloader 18 (shown in FIG. 1) advances the treatment wire 14 along the lumen 20 of the guide catheter 12. The treatment wire and the lumen are configured with adequate, but not excessive, radial clearance in order to prevent the treatment wire from becoming jammed within the lumen. Due to the clearance, the advancing treatment wire will normally bunch up such that it curves around the lumen excessively and does not extend into the lumen by an amount equal to the treatment wire's full length. The bunched up treatment wire thus follows a path down the lumen that does not necessarily parallel the central axis of the lumen, winding instead along the lumen on an indirect path having substantial radial and/or circumferential variation in position within the lumen.

Figure 4:
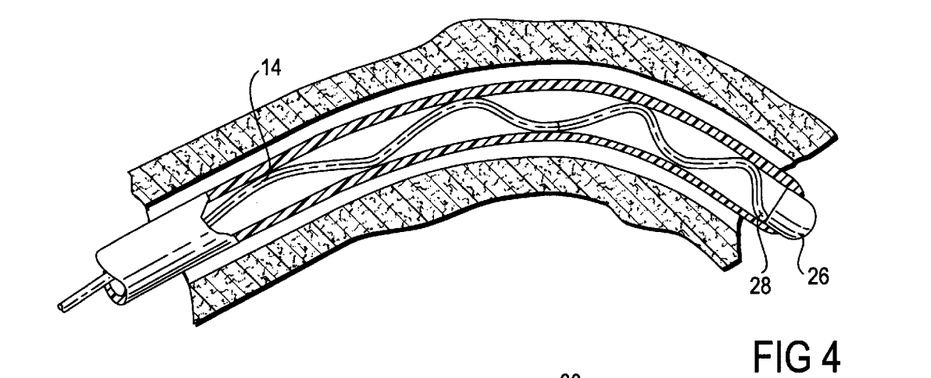
FIG. 4 is the cross-sectional view of the guide catheter depicted in FIG. 3, with the treatment wire fully inserted into the guide catheter such that it is contacting a distal tip of the guide catheter.

The treatment wire 14 advances along the lumen 20 until contacting the guide catheter's distal tip 26 at the distal end of the lumen, as depicted in FIG. 4. Prior to the treatment wire's contacting the guide catheter's distal tip, the treatment wire contacts only the non-conducting plastic walls of the guide catheter 12, and thus no electrical connection is made between the two leads 32, 34 of the monitoring device 16 (shown in FIG. 1). At the moment the distal tip 28 of the treatment wire contacts the distal tip of the guide catheter, an electrical circuit is completed between the two leads, the circuit having a signal path extending from the first lead through the treatment wire, the guide catheter's distal tip, the subject's body, and the external probe 36, to the second lead (shown in FIG. 1).

Throughout the procedure, the monitoring device 16 applies a voltage between the two leads 32, 34 in an attempt to sense a relatively low resistance along the signal path, which signifies the contact of the treatment wire 14 with the guide catheter's distal tip 26 (i.e., the sensor). In particular, the monitoring device is attempting to pass a preferably ac signal between the two leads. As described above, the electrical circuit is configured such that the signal path extends through a portion of the subject's body, without causing harm or discomfort to the subject. Upon the monitoring device's establishing that the treatment wire has reached the end of the lumen, and/or upon sensing that the afterloader is unable to advance the treatment wire further into the lumen 20, the computer controller commands the afterloader 18 to stop inserting the treatment wire 14 into the lumen.

Then, the afterloader begins a controlled withdrawal of the treatment wire 14 from the lumen 20. The monitoring device 16 monitors the signal through the sensor to determine when the predetermined portion of the treatment wire departs from the predetermined position within the lumen. As the treatment wire begins to withdraw, the excessively curved path of the bunched treatment wire is pulled to become relatively unbunched and straightened relative to the central axis of the lumen. The unbunched wire varies in radial and circumferential position within the lumen principally in response to the curved axial path of the lumen along the subject's vascular system, and to the stiffness of the wire. As the wire withdraws, the straightening of the treatment wire begins at the proximal end 22 of the guide catheter, and works its way toward the guide catheter's distal end 24.

Figure 5:
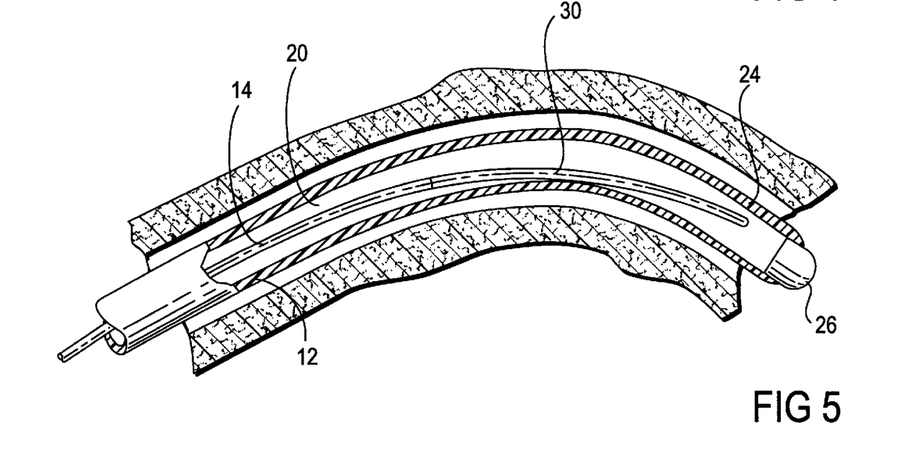
FIG. 5 is the cross-sectional view of the guide catheter depicted in FIG. 4, with the treatment wire having been controllably withdrawn from the guide catheter to the extent necessary to break the contact between the treatment wire and the distal tip of the guide catheter.

The controlled withdrawal is continued until the entire treatment wire 14 is straightened enough to remove the excess curvature, and then pulled out of contact with the guide catheter's distal tip 26, as is depicted in FIG. 5. At that moment the circuit formed along the signal path is broken (shown in FIG. 1). The monitoring device 16 (shown in FIG. 1) indicates to the computer controller that the circuit is broken, which then commands the afterloader to stop the controlled withdrawal. Preferably the controlled withdrawal is done at a high enough speed to position the wire quickly, but at a low enough speed to allow the withdrawal to be stopped before the treatment wire's distal tip 28 has been pulled significant distance from the guide catheter's distal tip.

The radioactive treatment portion 30 is now properly positioned at the distal end 24 of the guide catheter 12 for radiation treatment. The radioactive treatment portion is extended to approximately its full length within the lumen 20, and does not contain the significant amounts of radial and circumferential variation in position that exist in a bunched treatment wire 14. The principal variation in radial and circumferential position remaining is due to the curvature of the guide catheter, as can be seen in FIG. 5.

Immediately after the controlled withdrawal is terminated, the treatment wire 14 is maintained at this position for a prescribed time period, calculated to provide the desired amount of irradiation to the vascular area 40 requiring radiotherapy. If the controlled withdrawal required a significant period of time (from the standpoint of irradiating the subject), then the withdrawal time period may be used in the calculation of the prescribed time period.

If the vascular area requires radiotherapy in more than one position, the treatment wire can be withdrawn by a prescribed amount, to position the radioactive treatment portion 30 at the next sequential position requiring treatment, and immediately thereafter, can be maintained at that position for a further prescribed time period calculated to provide the desired amount of radiation at that location. The wire can also be further withdrawn by prescribed amounts to additional positions, and immediately thereafter, maintained for prescribed periods of time, as needed. After the radioactive treatment portion has been positioned and maintained at each of the desired positions, the treatment wire is rapidly withdrawn from the lumen 20 by the afterloader 18. The guide catheter 12 can then be carefully removed from the subject.

From the foregoing description, it will be appreciated that the present invention provides a device and a related method for positioning a longitudinal portion of a wire within a guide catheter. While a particular form of the invention has been illustrated and described, it will be apparent that various modifications can be made without departing from the spirit and scope of the invention.

For example, in the above-described embodiment, the monitoring device monitors a signal path that includes a sensor (the guide catheter's distal tip) at the end of the lumen, and the subject's body. However, in a second, and equally preferred embodiment, the signal path could extend between the guide catheter's distal tip and the second lead via a wire implanted in the guide catheter, rather than through the subject's body.

Figure 6:
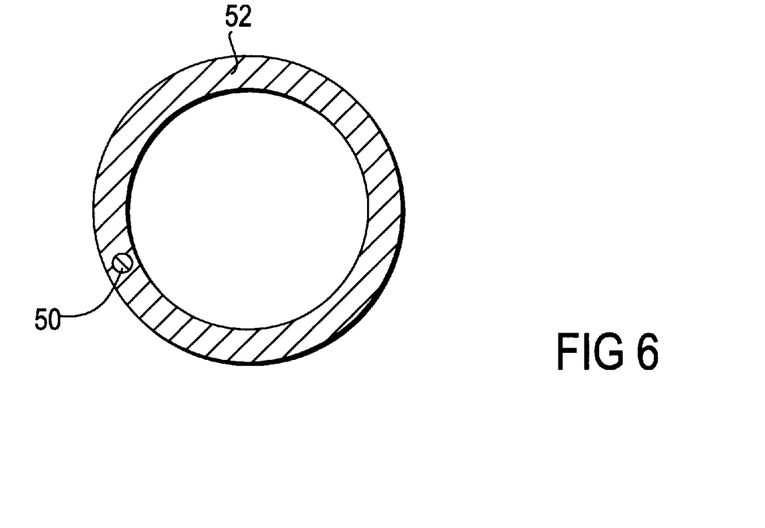
FIG. 6 is a cross-sectional view of a guide catheter from a second embodiment of a catheter assembly embodying features of the present invention.

In particular, the second embodiment is configured similarly to the first embodiment, but having the sensor connect to a conductor 50 extending longitudinally down substantially the entire length of a guide catheter 52, as seen in the axially-taken cross-section of the second embodiment's guide catheter depicted in FIG. 6. The conductor connects the guide catheter's distal tip, along with its exposed surface within the lumen, to the second lead, eliminating the need for the second lead to be connected to the subject. Thus, the monitored resistance is measured between the conductor and the proximal portion of the wire. Alternate versions of this embodiment could include a conductor extending along the guide catheter in a corkscrewed fashion, or even a conductor formed into a conductive layer within, or on the outside of, the guide catheter.

Figure 7A:
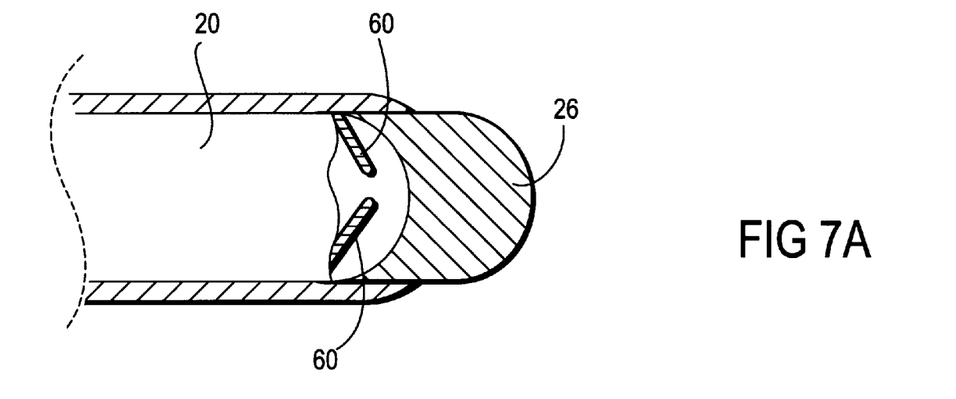
FIG. 7A is a radial cross-sectional view of a guide catheter from a third embodiment of a catheter assembly embodying features of the present invention.
Figure 7B:
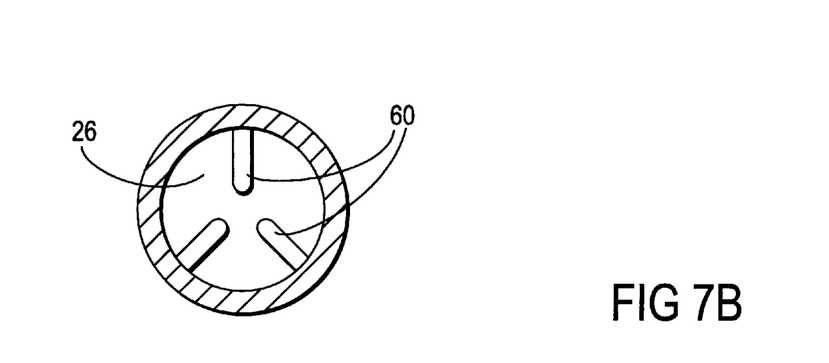
FIG. 7B is a longitudinal cross-sectional view of the guide catheter depicted in FIG. 7A.

A third embodiment of the invention may be configured similarly to either the first or the second embodiment, with the addition of a coupling mechanism that provides for superior sensing of the wire by the sensor. Preferably the coupling mechanism provides for superior electrical and/or mechanical contact between the wire and sensor. One preferred variation of a coupling mechanism, as depicted in FIGS. 7A and 7B, comprises a plurality of, and preferably three, conductive, flexible fingers 60 mounted symmetrically on the catheter's distal tip 26, which is concave rather than flat. The fingers are configured to receive the treatment wire's distal tip. The fingers are provided at an angle to the longitudinal direction of the lumen 20 so as to deflect when receiving the wire's distal tip, and allow the wire to move slightly without losing contact with the sensor. Depending on the angle of the fingers, they may also provide a gripping of the wire's distal tip, helping to hold the distal tip in place while the wire is becoming unbunched during withdrawal.

In other possible embodiments, the sensor need not detect an electrical connection, but rather can detect any physical property, such as mechanical, electrical, optical or chemical properties, that can indicate the presence of a portion of the treatment wire at a position along the guide catheter. Furthermore, the monitoring device can rely on any form of indicia that the sensor has detected presence of a portion of the treatment wire at a position along the guide catheter.

Additionally, in the described embodiment, the distal tip of the treatment wire served as the portion of the wire that the guide catheter detected. However, other portions of the treatment wire could serve as its predetermined portion, the presence of which is detectable by the guide catheter's sensor. Likewise, the sensor could be located at a position other than lumen's distal end.

While the treatment wire was described as a radiation source wire, the positioning of any wire to be inserted into the subject along a catheter is be within the scope of the invention. The wire may be configured for therapy, diagnosis, or other purposes. Furthermore, rather than a traditional guide catheter and radiation source wire, any configuration of catheters, where one longitudinally guides the other for treating a subject, is be within the scope of the invention, and the term wire is to be taken broadly so as to encompass all catheters to be received along another guiding catheter. In such an embodiment, the guiding catheter is understood to guide the treatment catheter by its participation in the monitoring devices establishing the presence of the treatment catheter's predetermined portion at the guiding catheter's predetermined position. The treatment catheter could itself be a guide catheter configured to receive another catheter within it.

Thus, although the invention has been described in detail with reference only to the preferred embodiments, those having ordinary skill in the art will appreciate that various modifications can be made without departing from the invention. Accordingly, the invention is not intended to be limited, and is defined with reference to the following claims.

We claim:

1. A method for positioning a wire in a selected portion of a subject's body, comprising:

providing a guide catheter having a lumen configured to receive the wire;

providing a sensor configured to detect the presence of a predetermined portion of the wire at a predetermined position within the lumen;

inserting the guide catheter to a selected location in the subject's body;

advancing the wire along the lumen;

monitoring the sensor to determine when the predetermined portion of the wire reaches the predetermined position within the lumen; and terminating the step of advancing the wire when it is determined, in the step of monitoring the sensor, that the predetermined portion of the wire has reached the predetermined position within the lumen.

2. The method defined in claim 1, wherein:

the step of inserting the guide catheter locates the guide catheter in a portion of the subject's cardiovascular system; and the wire is configured to treat the selected portion of the subject's body by irradiation.

3. The method defined in claim 1, wherein, in the step of providing a sensor, the sensor is integral with the guide catheter.

4. The method defined in claim 3, wherein:
the sensor comprises an electrical contact having an exposed surface within the lumen;
the wire is configured to be electrically conductive from a proximal portion to its predetermined portion; and
the step of monitoring the sensor comprises monitoring the resistance between the sensor and the proximal portion of the wire to determine when the predetermined portion of the wire and the sensor's exposed surface within the lumen come into contact.

5. The method defined in claim 4, wherein:
the predetermined portion of the wire, in the step of providing a wire, is at a distal tip of the wire; and
the sensor, in the step of providing a sensor, is located at a distal end of the guide catheter.

6. The method defined in claim 4, wherein:
the sensor, in the step of providing a sensor, includes an exposed surface on the exterior of the guide catheter that is electrically connected to the sensor's exposed surface within the lumen; and
the step of monitoring the resistance between the sensor and the proximal portion of the wire comprises monitoring the resistance between the subject's body and the proximal portion of the wire.

7. The method defined in claim 6, wherein the step of monitoring the resistance between the subject's body and the proximal portion of the wire comprises applying a varying voltage between the subject's body and the proximal portion of the wire to pass an ac signal between the subject's body and the proximal portion of the wire.

8. The method defined in claim 4, and further comprising providing a conductor that extends along substantially the entire length of the guide catheter and electrically connects to the sensor's exposed surface within the lumen, wherein, in the step of monitoring the resistance, the monitored resistance is measured across the conductor and the proximal portion of the wire.

9. The method defined in claim 1, and further comprising:
further monitoring the sensor to determine when the predetermined portion of the wire departs from the predetermined position within the lumen;
controllably withdrawing the wire from the lumen after the step of advancing the wire; and
terminating the step of controllably withdrawing the wire when it is determined, in the step of further monitoring the sensor, that the predetermined portion of the wire has departed from the predetermined position within the lumen.

10. The method defined in claim 9, and further comprising maintaining the wire in its position, for a prescribed period of time, after the step of terminating the step of controllably withdrawing the wire.

11. The method defined in claim 10, and further comprising:
withdrawing the wire from the lumen by a prescribed amount; and
maintaining the wire in its position, for a prescribed period of time, immediately after the completion of the step of withdrawing the wire from the lumen by a prescribed amount.

12. The method defined in claim 9, and further comprising:
withdrawing the wire from the lumen by prescribed amounts to one or more positions; and
maintaining the wire for prescribed periods of time at the one or more positions.

13. The method defined in claim 1, and further comprising
further monitoring the sensor to determine when the predetermined portion of the wire departs from the predetermined position within the lumen;
controllably withdrawing the wire from the lumen after the step of advancing the wire; and
terminating the step of controllably withdrawing the wire when it is determined, in the step of further monitoring the sensor, that the predetermined portion of the wire has departed from the predetermined position within the lumen;
wherein the sensor comprises an electrical contact having an exposed surface within the lumen;
wherein the wire is configured to be electrically conductive from a proximal portion to its predetermined portion; and
wherein the step of monitoring the sensor comprises monitoring the resistance between the sensor and the proximal portion of the wire to determine when the predetermined portion of the wire and the sensor's exposed surface within the lumen come into contact.

14. The method defined in claim 13, and further comprising:
maintaining the wire in its position for a prescribed period of time after the step of terminating the step of controllably withdrawing the wire;
withdrawing the wire from the lumen by a prescribed amount; and
maintaining the wire in its position, for a prescribed period of time, immediately after the completion of the step of withdrawing the wire from the lumen by a prescribed amount;
wherein the sensor, in the step of providing a sensor, includes an exposed surface on the exterior of the guide catheter that is electrically connected to the sensor's exposed surface within the lumen; and
wherein the step of monitoring the resistance between the sensor and the proximal portion of the wire further comprises monitoring the resistance between the subject's body and the proximal portion of the wire by applying a varying voltage between the subject's body and the proximal portion of the wire to pass an ac signal between the subject's body and the wire.

15. A method for positioning a wire in a selected portion of a subject's body, comprising:
providing a guide catheter having a lumen configured to receive the wire;
providing a sensor configured to detect the presence of a predetermined portion of the wire at a predetermined position within the lumen;
inserting the guide catheter to a selected location in the subject's body;
advancing the wire along the lumen;
terminating the step of advancing the wire when the predetermined portion of the wire has reached the predetermined position within the lumen;
monitoring the sensor to determine when the predetermined portion of the wire departs from the predetermined position within the lumen;
controllably withdrawing the wire from the lumen after the step of advancing the wire; and terminating the step of controllably withdrawing the wire when it is determined, in the step of monitoring the sensor, that the predetermined portion of the wire has departed from the predetermined position within the lumen.

16. The method defined in claim 15, and further comprising maintaining the wire in its position, for a prescribed period of time, after the step of terminating the step of controllably withdrawing the wire.

17. The method defined in claim 16, and further comprising:

withdrawing the wire from the lumen by a prescribed amount; and maintaining the wire in its position, for a prescribed period of time, immediately after the completion of the step of withdrawing the wire from the lumen by a prescribed amount.

18. The method defined in claim 15, and further comprising:

withdrawing the wire from the lumen by prescribed amounts to one or more positions; and maintaining the wire for prescribed periods of time at the one or more positions.

19. A catheter apparatus for use within a subject, comprising:

a guide catheter sized to be insertable within a subject, the guide catheter including a lumen extending into the guide catheter;

a wire sized to be insertable into the guide catheter's lumen to a predetermined position;

a sensor of the guide catheter configured to detect the presence of a predetermined portion of the wire at a predetermined longitudinal position along the guide catheter; and a monitoring device configured to monitor the sensor to determine when the predetermined portion of the wire is present at the predetermined position along the guide catheter.

20. The catheter apparatus defined in claim 19, wherein the wire is configured with a radioactive portion proximate its predetermined portion, for irradiating a selected portion of a subject's body.

21. The catheter apparatus defined in claim 19, wherein:

the wire is configured to be electrically conductive from its predetermined portion to a portion configured to be connected to the monitoring device;

wherein the sensor is an electrical contact having a surface exposed within the lumen at the predetermined position, to detect the presence of the predetermined portion of the guide catheter; and wherein the monitoring device is configured to monitor a signal path extending from its connection to the wire to the sensor.

22. The catheter apparatus defined in claim 21, wherein the monitoring device connects to the patent's body, and wherein sensor has an exposed surface on the exterior of the guide catheter to extend the signal path through the subject's body back to the monitoring device.

23. The catheter apparatus defined in claim 21, wherein the sensor further comprises a conductor that extends along substantially the entire length of the guide catheter and electrically connects the monitoring device to the surface exposed within the lumen.

24. The catheter apparatus defined in claim 19, wherein the sensor is located at a distal end of the guide catheter.

25. A catheter for use in positioning a wire in a selected portion of a subject's body, comprising a guide catheter sized to be insertable within a subject, wherein:

the guide catheter has surfaces forming a blind lumen that extends into the guide catheter;

the guide catheter is configured for receiving the wire into the lumen;

the guide catheter's surfaces that form the lumen are composed of a material that does not conduct electricity; and the guide catheter includes an electrical contact having an exposed surface within the lumen at a location within the subject's body.

26. The catheter defined in claim 25, wherein the electrical contact includes an exposed surface on the exterior of the lumen that is configured to contact the subject's body.

27. The catheter defined in claim 25, wherein the sensor further comprises a conductor that extends along substantially the entire length of the guide catheter and electrically connects the monitoring device to the exposed surface within the lumen.

28. A brachytherapy apparatus for irradiating a selected portion of a subject's body comprising:

a guide catheter sized to be insertable within the selected portion of the subject's body, the guide catheter including a lumen extending into the guide catheter;

a wire having a radioactive portion, the wire being sized to be insertable into the lumen such that the radioactive portion is proximate the selected portion of the subject's body when the guide catheter is inserted within the selected portion of the subject's body; and a sensor of the guide catheter configured to be located proximate the selected portion of the subject's body, the sensor being configured to detect the presence of a predetermined portion of the wire at a predetermined longitudinal position along the guide catheter.

29. The brachytherapy apparatus defined in claim 28, wherein the sensor is an electrical contact located at the predetermined longitudinal position along the guide catheter, the sensor being configured to complete an electrical signal path for detecting the presence of the predetermined portion of the wire at the predetermined longitudinal position along the guide catheter when the sensor is in contact with the predetermined portion of the wire.

30. The brachytherapy apparatus defined in claim 29, wherein the sensor includes a conductive surface exposed on the exterior of the guide catheter such that the signal path can pass through the subject's body to the monitoring device.

31. The brachytherapy apparatus defined in claim 29, wherein the sensor further comprises a conductor that extends along substantially the entire length of the guide catheter and electrically connects to the surface exposed within the lumen.

32. The brachytherapy apparatus defined in claim 28, wherein the sensor is located at a distal end of the guide catheter.

33. A method for treating a subject, comprising:

providing a treatment catheter configured to treat the subject;

providing a guiding catheter;

providing a sensor configured to detect the presence of a predetermined portion of the treatment catheter at a predetermined position along the guiding catheter;

inserting the guiding catheter to a selected location in the subject's body;

advancing the treatment catheter along the guiding catheter;

monitoring the sensor to determine when the predetermined portion of the treatment catheter reaches the predetermined position along the guiding catheter; and terminating the step of advancing the treatment catheter when it is determined, in the step of monitoring the sensor, that the predetermined portion of the treatment catheter has reached the predetermined position along the guiding catheter.

34. The method defined in claim 33, and further comprising further monitoring the sensor to determine when the predetermined portion of the treatment catheter departs from the predetermined position along the guiding catheter;

controllably withdrawing the treatment catheter from along the guiding catheter after the step of advancing the treatment catheter; and terminating the step of controllably withdrawing the treatment catheter when it is determined, in the step of further monitoring the sensor, that the predetermined portion of the treatment catheter has departed from the predetermined position along the guiding catheter.

35. The method defined in claim 34, and further comprising:

withdrawing the treatment catheter from along the guiding catheter by a prescribed amount; and maintaining the treatment catheter in its position, for a prescribed period of time, immediately after the completion of the step of withdrawing the treatment catheter from along the guiding catheter by a prescribed amount.

* * * * *